US006325511B1

(12) United States Patent
Mizuochi

(10) Patent No.: US 6,325,511 B1
(45) Date of Patent: Dec. 4, 2001

(54) OPHTHALMIC PHOTOGRAPHIC APPARATUS

(75) Inventor: Masaharu Mizuochi, Hamamatsu (JP)

(73) Assignee: Kowa Company Ltd. (JP)

( * ) Notice: Subject to any disclaimer, the term of this patent is extended or adjusted under 35 U.S.C. 154(b) by 0 days.

(21) Appl. No.: 09/563,061

(22) Filed: Apr. 24, 2000

(51) Int. Cl.[7] .................................................. A61B 3/14
(52) U.S. Cl. ................................................. 351/206
(58) Field of Search ................................ 351/205, 206, 351/211, 212; 396/18; 250/458.1, 459.1

(56) References Cited

U.S. PATENT DOCUMENTS 5,220,360 * 6/1993 Verdooner et al. ................ 351/212
5,630,179 * 5/1997 Kishida ............................... 396/18

* cited by examiner

Primary Examiner—George Manuel
(74) Attorney, Agent, or Firm—Adam & Wilks

(57) ABSTRACT

When fluorescent photography is initiated, a mode switching signal is sent to the image processing section to change the image processing mode to monochrome processing. At the same time, a timer is started that indicates the time elapsed since the fluorescent agent was administered. While the timer is on, fundus images acquired are converted to monochrome images by the image processing section and displayed on a monitor and stored in an image storage device. When the system enters fluorescent photography mode, images are converted to monochrome images automatically. This eliminates the need for a mode switching operation using a mode conversion button or the like to switch from color mode to monochrome mode.

12 Claims, 1 Drawing Sheet

OPHTHALMIC PHOTOGRAPHIC APPARATUS

BACKGROUND OF THE INVENTION

1. Field of the Invention

The present invention relates to an ophthalmic photographic apparatus, and more particularly to an ophthalmic photographic apparatus being capable of providing electronic fluorescent photographic images.

2. Description of the Prior Art

An eye fundus camera is an example of this type of ophthalmic photographic apparatus. With an eye fundus camera such as a CCD video camera, images of the eye fundus are obtained and processed to be displayed on a monitor and/or stored in an external storage device. When the eye fundus images obtained are fluorescent images, the images are displayed and/or stored not as color images but as monochrome images.

The above-described eye fundus camera has a number of drawbacks. For example, since fundus images obtained with the eye fundus camera described above are to be stored as monochrome images, a mode conversion button provided on the operation section or image processing section has to be operated to change the mode from color mode to monochrome mode. If, therefore, the operator should forget to change the mode back to color mode for conducting color photography instead of fluorescent photography, it will not be possible to obtain color images. Or, conversely, if the operator should forget to change the mode to monochrome mode during fluorescent photography, the fluorescent photographic images will be obtained and stored as ordinary color images, which afterwards will therefore have to be converted to monochrome images. A further problem is that when photographing many fluorescent images one after another, the conversion process takes time and effort and requires increased system storage capacity.

SUMMARY OF THE INVENTION

The object of this invention is therefore to overcome the problems of the prior art by providing an ophthalmic photographic apparatus that during fluorescent photography of the eye fundus is able to ensure the storage of the eye fundus images as monochrome images.

In accordance with the present invention, the above object is attained by an ophthalmic photographic apparatus being capable of providing electronic fluorescent photographic images, comprising means for detecting fluorescent photography, means for converting to monochrome images eye fundus photographic images acquired following the detection of fluorescent photography, and means for storing the eye fundus images converted to monochrome images.

In accordance with the apparatus of the invention, fluorescent photography is detected and fundus images acquired are then processed automatically to monochrome images. This eliminates the need for a mode switching operation using a specially provided mode conversion button or the like to switch from color mode to monochrome mode, and this also prevents inadvertent omission of switching to or from a mode.

The apparatus of the invention also includes a timer provided to measure the time that has elapsed from the time a fluorescent agent was administered. The operation of the timer signifies that the photography taking place is fluorescent photography, so fundus images acquired during timer operation are converted to monochrome images. Since in this arrangement the timer operated at the time the fluorescent agent is administered is used to signify that the photography taking place is fluorescent photography, eye fundus images acquired while the timer is in operation are converted to monochrome images automatically without needing any mode conversion button.

BRIEF DESCRIPTION OF THE DRAWINGS

This and other objects and advantages of the invention will be more apparent from the following description and drawings, in which.

DESCRIPTION OF THE PREFERRED EMBODIMENT

Figure 1:
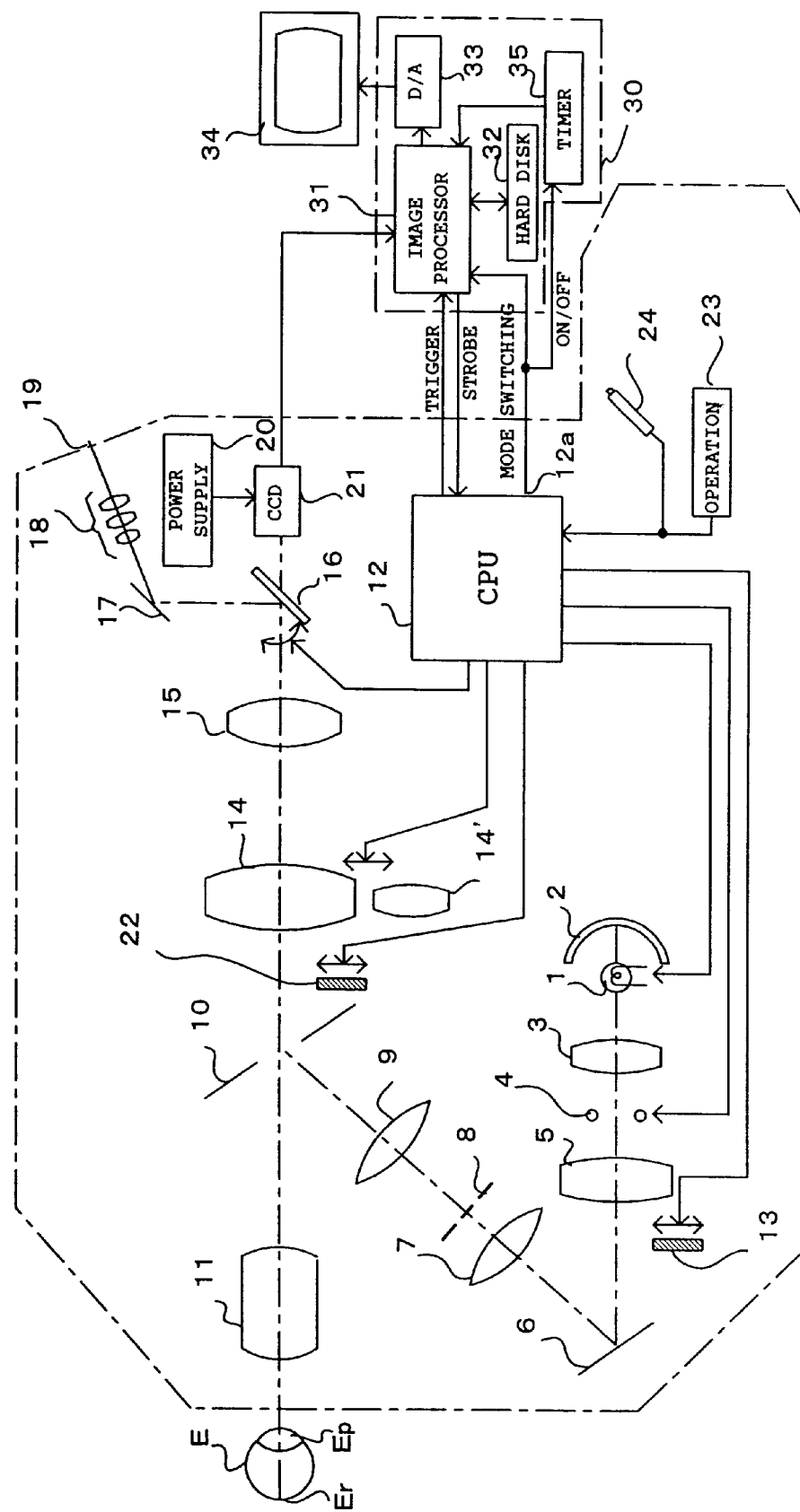
FIG. 1 is a schematic diagram showing an ophthalmic photographic apparatus of the invention.

In FIG. 1 there is shown an ophthalmic photographic apparatus according to the invention, particularly an eye fundus camera, in which a lamp 1 constituting an observation light source is disposed at the center of a mirror 2. Light from the lamp 1 passes through a condenser lens 3, a strobe 4 constituting a photographic light source, and a condenser lens 5, and is reflected by a total reflection mirror 6. The light thus reflected passes through a lens 7, a ring slit 8 used to form ring-shaped illumination, a relay lens 9, and is reflected by a total reflection mirror 10 having a center aperture. From the total reflection mirror 10, the light passes through an objective lens 11 and through a pupil Ep of a subject eye E to fall incident on the eye fundus Er. The lamp 1 and strobe 4 can be operated by means of signals from a CPU 12.

An exciter filter 13 for fluorescent photography can be removably inserted into the light path on the downstream side of the condenser lens 5. The exciter filter 13 transmits light having a wavelength of from 470 to 510 nm. During fluorescent photography, under the control of the CPU 12 the exciter filter 13 is inserted into the light path, and when the fundus is being observed or photographed the exciter filter 13 is removed from the light path.

Reflected light from the eye fundus Er passes back through the pupil Ep, the objective lens 11, the aperture in the total reflection mirror 10 and a relay lens 15 and falls incident on a return mirror 16. In accordance with signals transmitted by the CPU 12, either of variable power lenses 14 and 14' can be inserted into the light path to change the angle of view when observing or photographing the fundus. During observation of the fundus the return mirror 16 is inserted into the position shown in the drawing and during fundus photography the return mirror 16 is withdrawn from the light path under the control of the CPU 12. During observation, eye fundus images are guided to an observation section 19 by a mirror 17 and a set of lenses 18 to allow an examiner to examine the fundus. During photography, fundus images impinge on a CCD camera 21 driven by a power supply 20 to thereby enable the fundus images to be recorded.

A barrier filter 22 is provided on the light path downstream from the total reflection mirror 10. The barrier filter 22 blocks light having a wavelength below 530 nm and transmits wavelengths from 530 nm to 650 nm. Under the control of the CPU 12, the barrier filter 22 can be inserted into the light path when a shutter 24 is operated, but it can also be inserted beforehand by the examiner.

Fundus images obtained by the CCD camera 21 are input as color video signals to an image processing section 31 of an image processing unit 30 comprised by, for example, a personal computer. After processing the images are output, via a D/A converter 33, to a monitor 34. The eye fundus images processed by the image processing section 31 are also stored on a hard disk or other such image storage device 32.

When a fluorescent photography button (not shown) on an operation section 23 is operated, at output 12a the CPU 12 generates a signal that is input to the image processing section 31 as a mode switching signal, whereby the images in the image processing section 31 are converted to monochrome images. At the same time, the signal produced from the output 12a starts a timer 35. Since the fluorescent agent is administered at virtually the same time as the operation of the fluorescent photography button, the timer 35 indicates the time that has elapsed since the administration of the fluorescent agent. The time indicated by the timer 35 can be combined with the monochrome images in the image processing section 31 and, via the D/A converter 33, displayed on the monitor 34 together with the fundus images.

In operation, during observation of the fundus the return mirror 16 is inserted into the position shown in the drawing and the fundus Er is illuminated by the lamp 1. The observation section 19 can be used to observe the fundus thus illuminated, and for aligning the apparatus.

To conduct fluorescent photography, the fluorescent agent is administered to the subject and the fluorescent photography button on the operation section 23 is operated. This causes the CPU 12 to produce a signal from output 12a notifying the image processing section 31 of the change from color processing to monochrome processing. At the same time, the signal from output 12a also starts the timer 35, providing measurement of time elapsed from the administration of the fluorescent agent.

The exciter filter 13 and barrier filter 22 are inserted into the light path to observe the fundus or align the system. When preparations for fluorescent photography are complete, the shutter 24 is operated and the return mirror 16 is retracted from the light path, the CPU 12 sends a signal to the exciter filter 13 and to the barrier filter 22. This causes the filters not yet on the light path to be inserted into the light path. The operation of the shutter 24 causes the CPU 12 to output a trigger signal to the image processing section 31 that starts the intake of video signals from the CCD camera 21. Simultaneously with this, the image processing section 31 outputs a strobe activation signal to the CPU 12, causing the CPU 12 to activate the strobe 4. While light is being emitted by the strobe 4, fundus images are acquired by the CCD camera 21 and input as a video signal to the image processing section 31. The image processing section 31 converts the fundus images to a monochrome signal, stores the images in the image storage device 32 and, via the D/A converter 33, displays the images on the monitor 34.

The same series of operations takes place each time the shutter 24 operates, enabling fluorescent photography of multiple fundus images. Upon completion, the fluorescent photography button is again operated. This causes the CPU 12 to output a signal from output 12a that switches the image processing section 31 to color conversion mode and switches off the timer 35.

In accordance with the invention, operating the fluorescent photography button also triggers the timer, so the operation of the timer is used to detect or determine that the photography is fluorescent photography. However, the activation signal resulting from the operation of the fluorescent photography button can itself be used as means for detecting fluorescent photography. Similarly, fluorescent photography can be detected by shutter operation, or by insertion of a barrier filter, or other such means.

As described in the foregoing, in accordance with this invention, when it is detected that photography is fluorescent photography, images thus acquired by the fluorescent photography can be automatically converted to monochrome images and stored. This means that there is no need to switch modes at the operation section, and there is no risk of forgetting to switch to the proper mode. Moreover, large numbers of fluorescent images can be photographed with ensured conversion to monochrome images, thus providing the advantage that no large storage capacity is required.

What is claimed is:

1. An ophthalmic photographic apparatus capable of providing electronic fluorescent photographic images, comprising:

means for detecting when fluorescent photography is initiated and producing an output signal in response thereto;

means responsive to the output signal for converting to monochrome images eye fundus photographic images acquired following the detection of initiation of fluorescent photography; and means for storing the eye fundus images converted to monochrome images.

2. An apparatus according to claim 1; wherein the means for detecting includes a timer that measures time elapsed from administration of a fluorescent agent, the timer being activated in response to the output signal to detect initiation of fluorescent photography and cause eye fundus images acquired during timer operation to be converted to monochrome images.

3. In an ophthalmic photographic apparatus for selectively performing color photography and fluorescent photography of an eye fundus: a camera for recording color images or fluorescent images of an eye fundus and outputting corresponding color video signals or fluorescent video signals, depending on whether the apparatus is performing color photography or fluorescent photography; means for initiating fluorescent photography; means for detecting initiation of fluorescent photography and producing a mode switching signal; and an image processing section operable in a color processing mode for processing color video signals output by the camera to produce electronic color images and in a monochrome processing mode for processing fluorescent video signals output by the camera to produce electronic monochrome images, the image processing section being responsive to the mode switching signal to automatically change to the monochrome processing mode.

4. An ophthalmic photographic apparatus according to claim 3; wherein the means for initiating fluorescent photography comprises a fluorescent photograph button.

5. An ophthalmic photographic apparatus according to claim 4; wherein the means for detecting responds to operation of the fluorescent photograph button to produce the mode switching signal.

6. An ophthalmic photographic apparatus according to claim 5; wherein the means for detecting comprises a CPU.

7. An ophthalmic photographic apparatus according to claim 3; wherein the means for detecting responds to operation of a shutter of the ophthalmic photographic apparatus to produce the mode switching signal.

8. An ophthalmic photographic apparatus according to claim 7; wherein the means for detecting comprises a CPU.

9. An ophthalmic photographic apparatus according to claim 3; wherein the means for detecting responds to insertion of a filter into a light path of the ophthalmic photographic apparatus to produce the mode switching signal.

10. An ophthalmic photographic apparatus according to claim 9; wherein the means for detecting comprises a CPU.

11. An ophthalmic photographic apparatus according to claim 3; further including a storage device for storing the electronic monochrome images.

12. An ophthalmic photographic apparatus according to claim 3; further including a timer activated in response to the mode switching signal for measuring a predetermined elapsed time from initiation of fluorescent photography.

* * * * *